(12) United States Patent
Duchon et al.

(10) Patent No.: US 6,626,862 B1
(45) Date of Patent: Sep. 30, 2003

(54) FLUID MANAGEMENT AND COMPONENT DETECTION SYSTEM

(75) Inventors: Douglas J. Duchon, Chanhassen, MN (US); Robert F. Wilson, Roseville, MN (US); Jiyan Liu, Maplewood, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 09/542,422

(22) Filed: Apr. 4, 2000

(51) Int. Cl.$^7$ ................................................ A61M 5/00
(52) U.S. Cl. ................. 604/110; 604/152; 128/DIG. 13
(58) Field of Search ................................ 604/110, 247, 604/248, 65, 67, 137, 511, 512.1, 843, 152, 151, 155; 128/DIG. 1, DIG. 12, DIG. 13

(56) References Cited

U.S. PATENT DOCUMENTS

| | | |
|---|---|---|
| 1,495,924 A | 5/1924 | Quale |
| 1,704,921 A | 3/1929 | Nicoll |
| 3,157,201 A | 11/1964 | Littmann |
| 3,623,474 A | 11/1971 | Heilman et al. |
| 3,631,847 A | 1/1972 | Hobbs, II |
| 3,701,345 A | 10/1972 | Heilman et al. |
| 3,734,258 A | 5/1973 | Roob |
| 3,768,484 A | 10/1973 | Gawura |
| 3,768,518 A | 10/1973 | Roth et al. |
| 3,910,466 A | 10/1975 | Collar |
| 3,957,052 A | 5/1976 | Topham |
| 4,000,685 A | 1/1977 | Montalvo, Jr. |
| 4,006,736 A | 2/1977 | Kranys et al. |
| 4,267,836 A | 5/1981 | Whitney et al. |
| 4,366,831 A | 1/1983 | Scott |
| 4,367,736 A | 1/1983 | Gupton |
| 4,370,982 A | 2/1983 | Reilly |
| 4,444,198 A | 4/1984 | Petre |
| 4,452,251 A | 6/1984 | Heilman |
| 4,468,221 A | 8/1984 | Mayfield |
| 4,469,481 A | 9/1984 | Kobayashi |
| 4,475,666 A | 10/1984 | Bilbrey et al. |
| 4,502,488 A | 3/1985 | Degironimo et al. |
| 4,585,941 A | 4/1986 | Bergner |
| 4,594,073 A | 6/1986 | Stine |
| 4,596,558 A | 6/1986 | Smith et al. |
| 4,608,996 A | 9/1986 | Brown |
| 4,619,646 A | 10/1986 | Fernandez-Tresguerres Hernandez et al. |
| 4,661,096 A | 4/1987 | Teeple |
| 4,677,980 A | 7/1987 | Reilly et al. |
| 4,741,736 A | 5/1988 | Brown |
| 4,779,614 A | 10/1988 | Moise |
| 4,812,724 A | 3/1989 | Langer et al. |
| 4,842,576 A | 6/1989 | Lysaght et al. |
| 4,854,324 A | 8/1989 | Hirschman et al. |
| 4,865,581 A | 9/1989 | Lundquist et al. |
| 4,865,584 A * | 9/1989 | Epstein et al. ............... 604/258 |
| 4,903,705 A | 2/1990 | Imamura et al. |

(List continued on next page.)

FOREIGN PATENT DOCUMENTS

| | | |
|---|---|---|
| DE | 196 33 530 A1 | 2/1998 |
| EP | 0554716 A1 | 8/1993 |
| EP | 0567944 A1 | 11/1993 |

(List continued on next page.)

*Primary Examiner*—Edward K. Look
*Assistant Examiner*—Richard A. Edgar
(74) *Attorney, Agent, or Firm*—Kramer, Levin, Naftalis & Frankel

(57) ABSTRACT

Devices that detect and monitor components and fluid used with an injector system, such as an angiographic injector system, are disclosed. The devices may include mechanical, electrical or software based indexing or keying features to ensure that only compatible components are used on the system. In addition, these devices may also be used to track and/or monitor fluid volume and use during various injection procedures. Single use and multiple use components, conveniently supplied in kits, may also be tracked and/or monitored by the devices of the present invention.

23 Claims, 8 Drawing Sheets

U.S. PATENT DOCUMENTS

| | | | |
|---|---|---|---|
| 4,921,488 A | | 5/1990 | Maitz et al. |
| 4,923,443 A | * | 5/1990 | Greenwood et al. ........ 604/110 |
| 4,976,696 A | * | 12/1990 | Sanderson et al. ... 128/DIG. 12 |
| 4,978,335 A | * | 12/1990 | Arthur, III ............. 128/DIG. 1 |
| 4,994,065 A | | 2/1991 | Gibbs et al. |
| 5,006,110 A | | 4/1991 | Garrison et al. |
| 5,034,000 A | | 7/1991 | Freitas et al. |
| 5,053,002 A | | 10/1991 | Barlow |
| 5,055,005 A | | 10/1991 | Kletschka |
| 5,059,174 A | | 10/1991 | Vaillancourt |
| 5,078,683 A | | 1/1992 | Sancoff et al. |
| 5,084,011 A | | 1/1992 | Grady |
| 5,084,017 A | | 1/1992 | Maffetone |
| 5,104,387 A | | 4/1992 | Pokorney et al. |
| 5,112,200 A | | 5/1992 | Isaacson et al. |
| 5,137,514 A | | 8/1992 | Ryan |
| 5,176,658 A | | 1/1993 | Ranford |
| 5,178,609 A | | 1/1993 | Ishikawa |
| 5,244,463 A | | 9/1993 | Cordner, Jr. et al. |
| 5,246,012 A | | 9/1993 | Strickland |
| 5,261,883 A | | 11/1993 | Hood et al. |
| 5,340,364 A | | 8/1994 | Ghelli et al. |
| 5,342,298 A | | 8/1994 | Michaels et al. |
| 5,346,470 A | * | 9/1994 | Hobbs et al. ................. 604/24 |
| 5,351,523 A | | 10/1994 | Blackford et al. |
| 5,383,858 A | | 1/1995 | Reilly et al. |
| 5,417,213 A | | 5/1995 | Prince |
| 5,423,746 A | | 6/1995 | Burkett et al. |
| 5,472,403 A | | 12/1995 | Cornacchia et al. |
| 5,485,831 A | | 1/1996 | Holdsworth et al. |
| 5,496,559 A | | 3/1996 | Fujioka et al. |
| 5,515,851 A | | 5/1996 | Goldstein |
| 5,535,746 A | * | 7/1996 | Hoover et al. .............. 600/431 |
| 5,549,569 A | | 8/1996 | Lynn et al. |
| 5,556,384 A | | 9/1996 | da Encarnacão |
| 5,573,515 A | | 11/1996 | Wilson et al. |
| 5,593,385 A | * | 1/1997 | Harrison et al. ............... 604/83 |
| 5,643,211 A | | 7/1997 | Sadowski et al. |
| 5,658,252 A | | 8/1997 | Johnson |
| 5,672,155 A | | 9/1997 | Riley et al. |
| 5,722,956 A | * | 3/1998 | Sims et al. .......... 128/DIG. 12 |
| 5,795,333 A | * | 8/1998 | Reilly et al. ................. 604/131 |
| 5,800,397 A | * | 9/1998 | Wilson et al. ......... 137/625.67 |
| 5,823,993 A | | 10/1998 | Lemelson |
| 5,840,026 A | * | 11/1998 | Uber et al. .......... 128/DIG. 12 |
| 5,843,037 A | | 12/1998 | Uber .......................... 604/151 |
| 5,871,692 A | * | 2/1999 | Haire et al. .................... 422/22 |
| 5,882,343 A | | 3/1999 | Wilson et al. |
| 5,885,216 A | * | 3/1999 | Evans et al. ................. 600/431 |
| 5,938,638 A | | 8/1999 | Passariello et al. |
| 6,099,502 A | * | 8/2000 | Duchon et al. ...... 128/DIG. 12 |
| 6,149,627 A | | 11/2000 | Uber .......................... 604/151 |
| 6,221,045 B1 | * | 4/2001 | Duchon et al. ........ 128/DIG. 1 |
| 6,306,117 B1 | | 10/2001 | Uber .......................... 604/151 |
| 6,344,030 B1 | * | 2/2002 | Duchon et al. ........ 128/DIG. 1 |
| 6,442,418 B1 | | 8/2002 | Evans ........................ 600/431 |

FOREIGN PATENT DOCUMENTS

| | | |
|---|---|---|
| WO | WO 88/03815 A1 | 6/1988 |
| WO | WO 92/18175 A1 | 10/1992 |
| WO | WO 93/15658 A1 | 8/1993 |
| WO | WO 96/32975 A1 | 10/1996 |
| WO | WO 97/07841 A2 | 3/1997 |
| WO | WO 99/21600 A2 | 5/1999 |
| WO | WO 99/24095 A2 | 5/1999 |

* cited by examiner

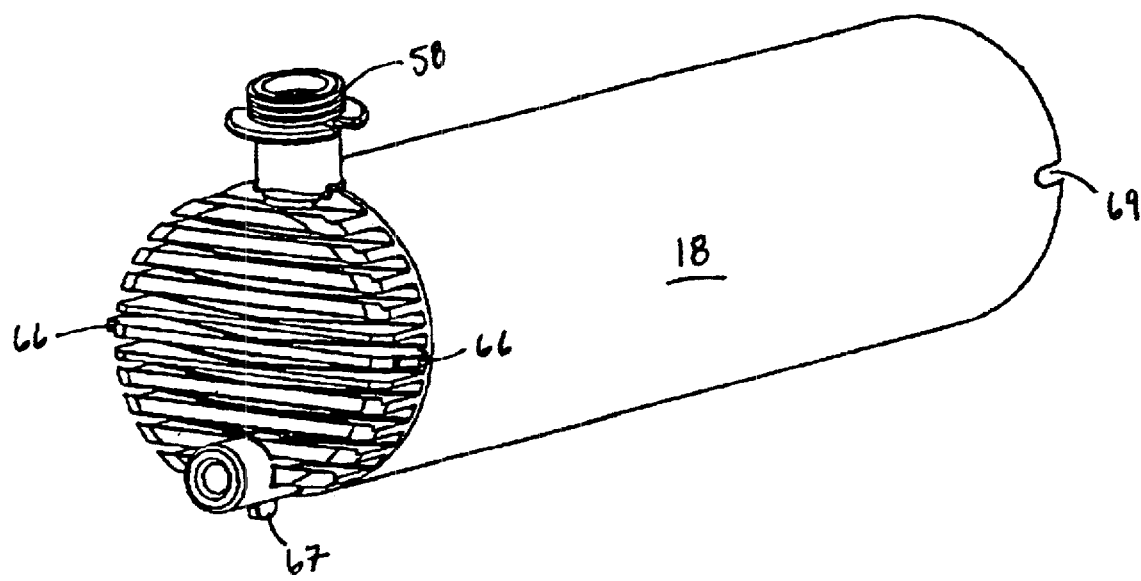
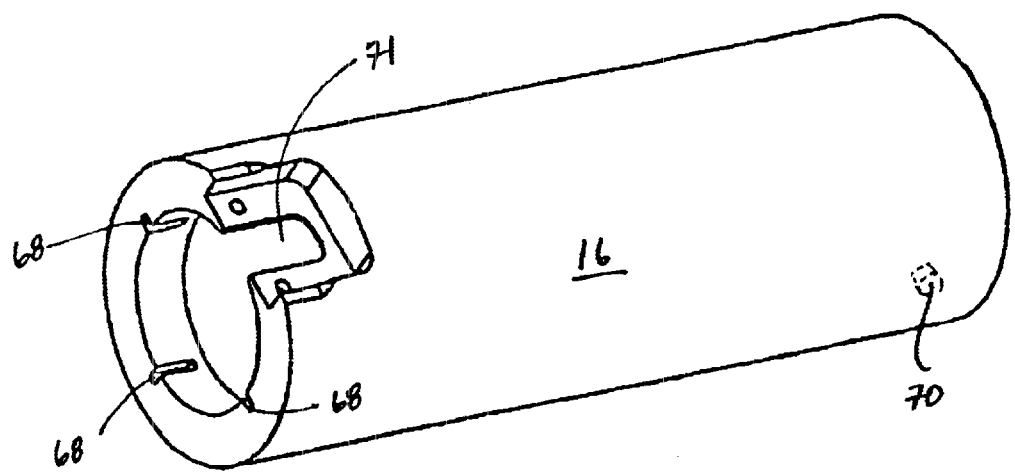
FIG. 4

FLUID MANAGEMENT AND COMPONENT DETECTION SYSTEM

FIELD OF THE INVENTION

The present invention relates to a fluid management and component detection system used during a surgical procedure. The present invention particularly relates to injector systems and devices used to detect and monitor injector components and fluids, such as contrast media, during an injection procedure.

BACKGROUND OF THE INVENTION

Angiography is a procedure used to specifically image, diagnose and treat abnormalities in the heart or vascular structures. In recent decades, radiologists, cardiologists and vascular surgeons have also used angiography procedures to guide minimally invasive surgery of the blood vessels and arteries of the heart. During angiography, a physician inserts a catheter and injects a contrast material into a vein or artery of a patient. The vascular structures fluidly connected with the vein or artery in which the injection occurred are subsequently filled with the contrast material. Next, the area of the patient's body injected with the contrast material is imaged using x-ray energy, whereby the radiation beam passes through the tissue of the patient and is absorbed by the contrast material. The resulting image or radiographic outline of the blood vessel is recorded onto film or videotape and/or displayed on a fluoroscope monitor. The images can be used for many purposes, as for example diagnostics and interventional procedures such as angioplasty, wherein a balloon is inserted into a vascular system and inflated to open a stenosis.

Various manual and automated injection systems used for performing angiography procedures are known in the art. Most current systems include a syringe and other disposable components (such as manifold tubing, spikes, etc.) operatively connected to a catheter. The syringe is filled by creating a vacuum which causes the contrast media to be suctioned into the chamber of the syringe. Any residual air is ejected from the chamber before connecting the syringe to the patient catheter. Once the system is completely set-up and primed, the syringe is connected to the patient catheter and the contrast media is injected into the target area.

The volume and flow rates of contrast media injections vary depending on patient parameters (such as heart/chamber/vasculature size, patient weight and physical condition) and type of treatment or diagnosis performed. Due to the variability of these parameters, it is often difficult to calculate the precise amount of contrast media needed for a particular patient and procedure. As a result, there exists the potential that the syringe chamber will be either under-filled or over-filled for a particular patient and/or procedure.

If the chamber is under-filled, an insufficient volume of contrast media will be injected into the patient, resulting in a less than optimal image and requiring that the procedure be repeated. This is not only expensive due to the high cost of contrast media, but is also potentially harmful to the patient in view of the additional radiation exposure and contrast dose injected into the patient. Conversely, if the syringe is over-filled, there will be an excess volume of contrast media remaining in the syringe after completion of the imaging procedure. To avoid patient contamination and product adulteration, the remaining volume of contrast media is simply discarded. Although over-filling the syringe avoids the problem of having to repeat the imaging procedure, over-filling wastes contrast media which is costly to hospitals and health care facilities.

Typically, contrast media is supplied in fluid volume containers having a 50 ml, 100 ml, 250 ml or 500 ml capacity. In contrast, patient procedures characteristically require as little as tens of milliliters to as much as hundreds of milliliters of fluid per procedure. The limited container volumes in conjunction with the variability associated with patient procedures often result in wasted fluid. For example, if a procedure requires 150 ml of fluid and a 250 ml container is used, the amount of fluid remaining in the container at the end of the procedure is discarded due to possible cross-contamination and fluid-crystallization issues. The discarded, unused portion not only wastes fluid, but also significantly contributes to increased hospital costs.

In addition to cost issues, the medical community is also faced with contamination problems associated with imaging procedures and, more particularly, the injector systems used to dispense the fluids. For example, the syringe, tubing and ancillary injector components used during imaging procedures are in fluid-communication with the patient. As a result, these items must be discarded after each case in order to avoid patient and/or product contamination, a potential risk confronting all products used during invasive procedures. Another reason for disposing of these items after a single use is that the majority of the imaging components are made of materials that are incompatible with state-of-the-art cleaning and resterilization procedures and, therefore, cannot be reused.

Although presently available injector systems are well accepted by the medical profession and function as required, it is desirable to have a more cost-effective injector system that is also safe and efficacious to use. In particular, it is desirable to have an injector system with a reservoir of contrast media that allows more than one patient to be injected using the same reservoir supply. It is also preferred that the system accommodate a variety of reservoir/container designs and fluids having various volumes, concentrations, viscosities, etc. It is also essential that the contrast media/fluid supply remain contamination-free during each use. In addition, it is desirable to have an injection system with a variety of accessory components that are single use, multiple use and resterilizable. Further, it is preferred that the system perform both diagnostic and non-diagnostic procedures, such as x-ray procedures. CT scanning, magnetic resonance imaging, ultrasonic imaging, angioplasty, saline ablation, etc., and is capable of using a variety of fluids, such as contrast media, saline, flushing fluids, etc.

OBJECTS AND SUMMARY OF THE INVENTION

In view of the foregoing, it is an object of the present invention to provide an injector subassembly that addresses the obstacles and disadvantages associated with current fluid injection practices.

A further object of the present invention is to provide an injector subassembly that is cost-effective, safe and efficacious to use.

A further object of the present invention is to provide an injector system with a reservoir of contrast media that allows more than one patient to be injected using the same reservoir supply.

A further object of the present invention is to provide a system that can accommodate a variety of reservoir/container designs and fluids having various volumes, concentrations, viscosities, etc.

A further object of the present invention is to provide a system wherein the contrast media/fluid supply remain contamination free during each use.

The present invention attempts to address these objects and other objects not specifically enumerated herein through the use of an injector subassembly used with an injector system, wherein the injector subassembly comprises a single use portion and a multiple use portion. In particular, the single use portion is fluidly connected to the multiple use portion, and the single use portion includes a high pressure tube connected to a catheter connection and the multiple use portion includes a syringe connected to a fluid supply reservoir. Further, the syringe and high pressure tube of the system are configured to be in fluid communication at a predetermined period of operation.

Another embodiment of the present invention contemplates an injector subassembly wherein a length of the high pressure tube is related to a pressure drop along the length of the tube.

Another embodiment of the present invention contemplates a multiple use portion that can be reused up to approximately five times.

Another embodiment of the present invention contemplates a multiple use portion that can be reused on one or more patients without cleaning or sterilizing the multiple use portion between each use.

Another embodiment of the present invention contemplates a single use portion that is supplied to a user of the subassembly as a kit.

Another embodiment of the present invention contemplates a multiple use portion that is supplied to a user of the subassembly as a kit.

The present invention also contemplates a syringe for use in an angiographic injector system, wherein the syringe comprises a syringe body having a distal end, a proximal end and a pumping chamber. In addition, a syringe plunger is located in the pumping chamber of the syringe and is movable along a path from the distal end to the proximal end of the syringe body. Further, the syringe plunger is connected to and controlled by a user-interface subassembly whereby the syringe plunger automatically disconnects from the syringe body when the syringe body has been used for a maximum number of uses.

The present invention also contemplates an angiographic injector system that tracks the volume of fluid injected into a patient or dispensed by the system, wherein the injector system comprises a user-interface subassembly and a reservoir containing fluid used during an injection procedure. In addition, the system includes a syringe fluidly connected to the reservoir and a patient, wherein the syringe includes a syringe plunger movable within the syringe. Further, the system also includes a syringe holder that holds the syringe in place on the injector system, whereby the syringe holder includes at least one electrical device that tracks the volume of fluid dispensed by the syringe via movement of the syringe plunger.

The present invention also contemplate an angiographic injector system comprising an injector subassembly and a user-interface subassembly wherein the user-interface subassembly includes a resume feature that allows for the recovery of the system from an error condition or power down.

BRIEF DESCRIPTION OF THE DRAWINGS

FIG. 4 is a perspective view of the syringe body and the syringe holder of the angiographic injector system in accordance with a preferred embodiment of the present invention;

DETAILED DESCRIPTION

Figure 1:
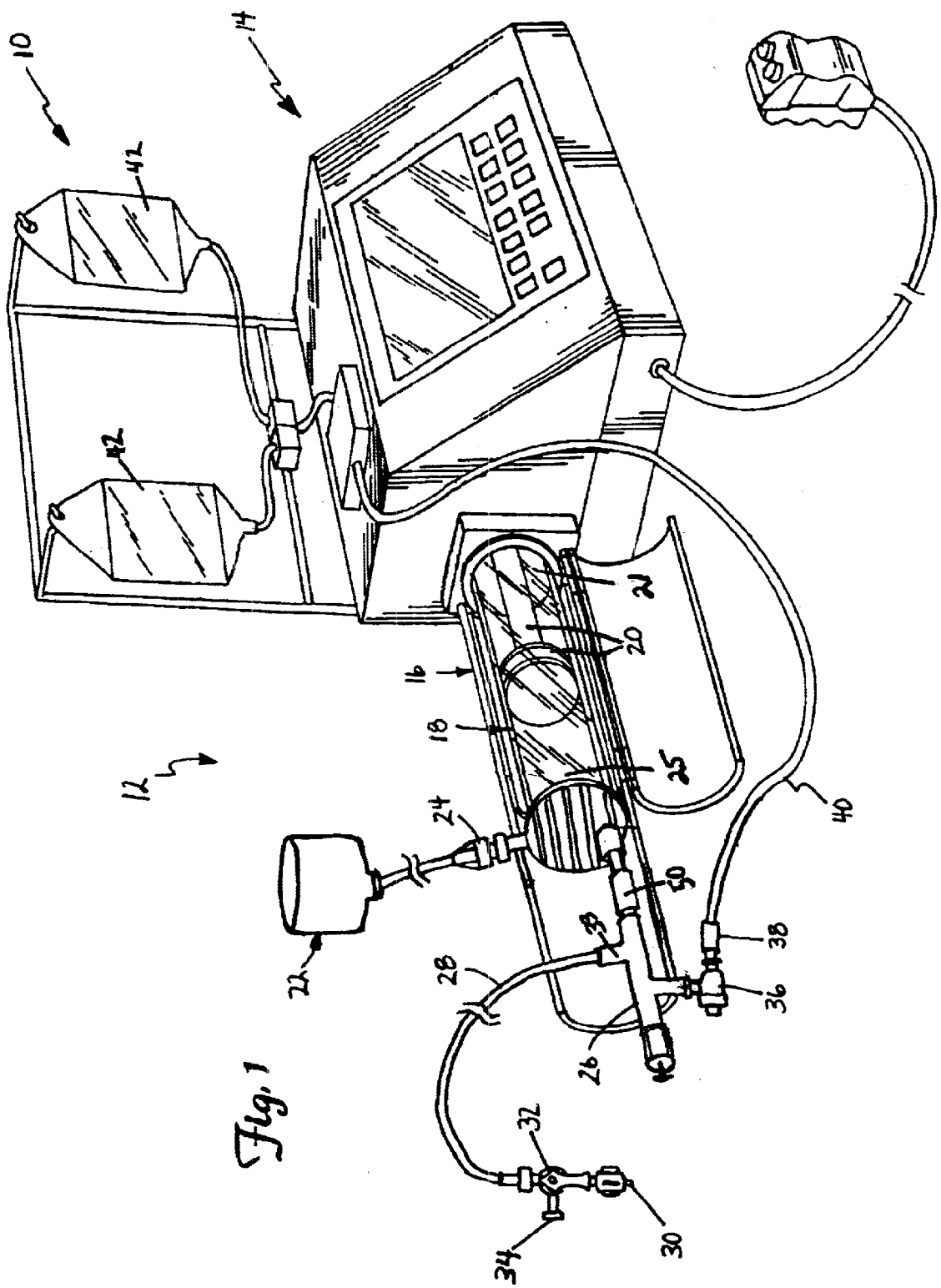
FIG. 1 is a perspective view of an angiographic injector system in accordance with a preferred embodiment of the present invention.

Referring to FIG. 1, an embodiment of an angiographic injector system 10 used to inject radiographic contrast material into a blood vessel under interactive physician control in accordance with the present invention includes an injector subassembly 12 and a user-interface subassembly 14. For an example of a compatible user-interface subassembly 14, the reader is referred to application Ser. No. 08/957,228, filed on Oct. 24, 1997, and which is hereby incorporated by reference in its entirety into the present application.

The injector subassembly 12 includes a syringe holder 16 used to house a syringe body 18. Located within the syringe body 18 is a detachable syringe plunger 20. When moved toward the proximal end 21 of the syringe body 18, the syringe plunger 20 creates a pressure differential in the syringe body 18 which draws contrast material from the radiographic material reservoir (bottle) 22, through the one-way valve 24 and into the syringe body 18. When the syringe plunger 20 is moved toward the distal end 25 of the syringe body 18, contrast material exits the syringe body 18 via the interconnection luer 50 and enters the patient manifold (check valve) 26. From the patient manifold 26, the contrast material enters the patient port 33 and flows through the high pressure tube 28 into the three-way stop-cock 32 and toward the catheter connection 30.

Figure 2:
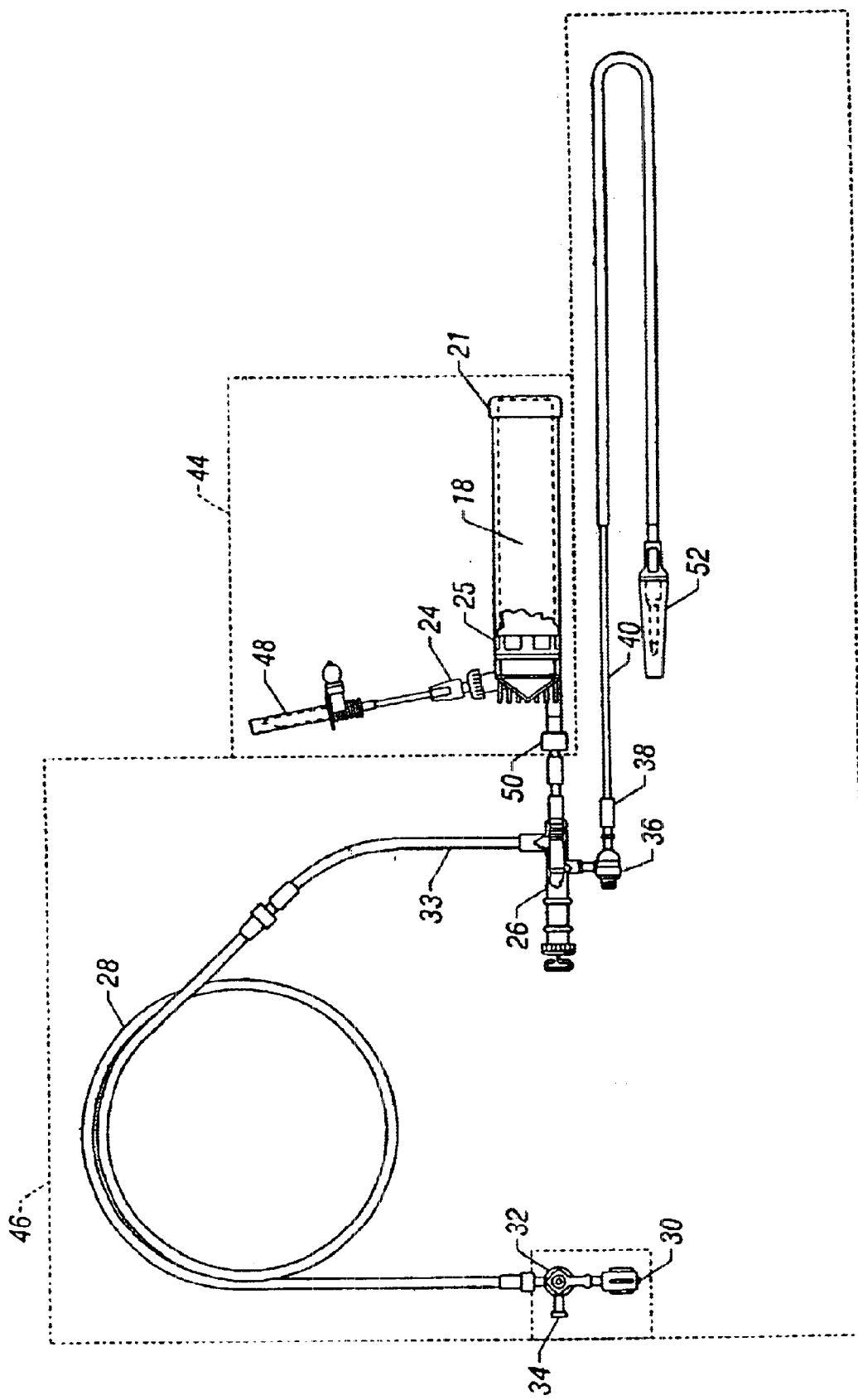
FIG. 2 is a perspective view of the injector subassembly of the angiographic injector system in accordance with a preferred embodiment of the present invention.

As shown in FIG. 2, a preferred embodiment of the injector subassembly 12 of the present invention includes a multiple use portion 44 and a single use portion 46. The components comprising the single use portion 46 and multiple use portion 44 are supplied to the user in discrete kit configurations that are safe, effective, sterile and easy to use. An individual kit comprising the single use components 46 may be used for cardiology, radiology, ultrasound, magnetic imaging, computed tomography or similar procedures. This multifunctional design aspect of the single use components 46 provides additional cost savings and safety benefits to users of the device.

In particular, given that one kit can be used for a variety of procedures, the potential of using incompatible components during a given procedure is significantly reduced or eliminated altogether. In addition, the single use, multifunctional kit allows for component standardization, especially for physicians that may practice at numerous facilities, and reduces the number of components that need to be inventoried by hospitals and health care facilities, thereby providing additional cost benefits and contributing to user convenience.

The components of the single use kit 46 may be manufactured from a variety of materials such as thermoplastics, specifically PVC, ABS, polypropylene, polyethylene, polyurethane, polycarbonate, etc., and/or elastomeric thermosets, such as polyisoprene, nitrile rubber, EPDM, silicone rubber, and other similar materials. Therefore, after each patient procedure or use, the single use components 46 are simply disconnected from the angiography system 10 and conveniently discarded.

In contrast, the components comprising the multiple use kit 44 may be reused on one or more patients or cases. In a preferred embodiment, the components of the multiple use kit 44 are made of the same or similar materials as the single use kit and can be reused up to approximately five times. Since the multiple use components 44 are reusable, they may be more cost effective for hospitals or medical facilities than single use components 46.

Referring to FIG. 2, the components comprising the single use portion 46 or kit include the patient manifold 26, patient port 33, high pressure tube 28, catheter connection 30, three-way stop-cock 32, patient medication port 34, pressure transducer 36, saline check valve 38, saline tubing 40 and saline spike 52.

The patient manifold 26 includes a spring biased spool valve which normally connects the pressure transducer 36 and the patient port 33. However, during an injection procedure, pressure from the contrast material in the syringe biases the spool valve of the patient manifold 26 to change states so that the lower port 50 of the syringe body 18 connects to the patient port 33. The pressure required to actuate the spool valve is variable and may be set by the manufacturer of the device by increasing or decreasing the characteristics of the spring.

In addition to controlling the direction of fluid flow, the patient manifold 26 also functions as a mechanism to prevent patient and/or system contamination during an injection procedure. The patient manifold 26 provides a fluid connection for the patient port 33, the pressure transducer 36 and the syringe 18. As such, the patient manifold 26 serves as a check valve to prevent retrograde flow of patient fluid to the syringe 18 and/or pressure transducer 36, thereby maintaining contamination-free fluid flow paths among the various system components.

The high pressure tube 28 of the present invention connects the patient port 33 to the three-way stop-cock 32. In a preferred embodiment, the high pressure tube 28 is made of PVC. However, alternative materials, such as reinforced urethane, can also be used. As used on the system of the present invention, the length of the high pressure tube 28 is directly related to the amount of pressure drop between the patient port 33 and the stop-cock 32. In a preferred embodiment, the high pressure tube 28 is 111.76 ±0.32 cm in length. However, various lengths for the high pressure tube 28 may also be used provided that the system maintains adequate pressure during the specified procedure.

As shown in FIG. 2, the three-way stop-cock 32 of the present invention regulates the flow of fluid to and from the patient. In its first or off position, the stop-cock 32 prevents any fluid from flowing into or out of the patient. When the stop-cock 32 is adjusted to its second position, the stop-cock 32 is open to allow fluid to flow from the high pressure tube 28, via the stop-cock 32, through the catheter connection 30 and into the patient. As such, the stop-cock 32 is rotated to selectively occlude one port and allow communication between the remaining two ports.

In some instances, it is desirable to inject the patient with medicaments or aspirate out patient fluids without having a separate injection site in addition to the patient catheter site. In these situations, the stop-cock 32 is turned to its third position. Opening the stop-cock 32 to its third position allows medication to be injected into the patient medication port 34, through the stop-cock 32 and into the patient via the catheter connection 30. The patient medication port 34 can also be used to aspirate fluids from the patient as for blood sampling and similar procedures.

Often during a medical procedure, more than one type of fluid injection is desired, such as a saline flush followed by the radiographic contrast material. For this procedure, saline is pumped from a saline supply 42 to the saline tubing 40, through the saline check valve 38 and into the pressure transducer 36. The pressure transducer 36 allows for removal/expulsion of trapped air so the dome chamber of the pressure transducer 36 can be flushed with saline. The saline then flows from the pressure transducer 36, through the patient manifold 26, into the patient port 33 and through the high pressure tubing 28. Once the saline enters the high pressure tubing 28, the saline follows the same fluid path of the contrast media as described above.

In a preferred embodiment, the components of the single use portion 46 are disposable, single use items that are replaced after each patient or case. However, in an alternate embodiment, these components may be cleaned and resterilized after each patient/case and reused.

As shown in FIG. 2, the multiple use portion 44 or kit comprises the syringe body 18, one-way valve 24, fluid/contrast container spike 48, interconnection luer 50, saline tubing 40 and saline spike 52. The multiple use portion 44 allows for the continuous use of contrast media for multiple patients/cases, while maintaining sterility of the contrast media supply and preventing inter-patient contamination.

Figure 3:
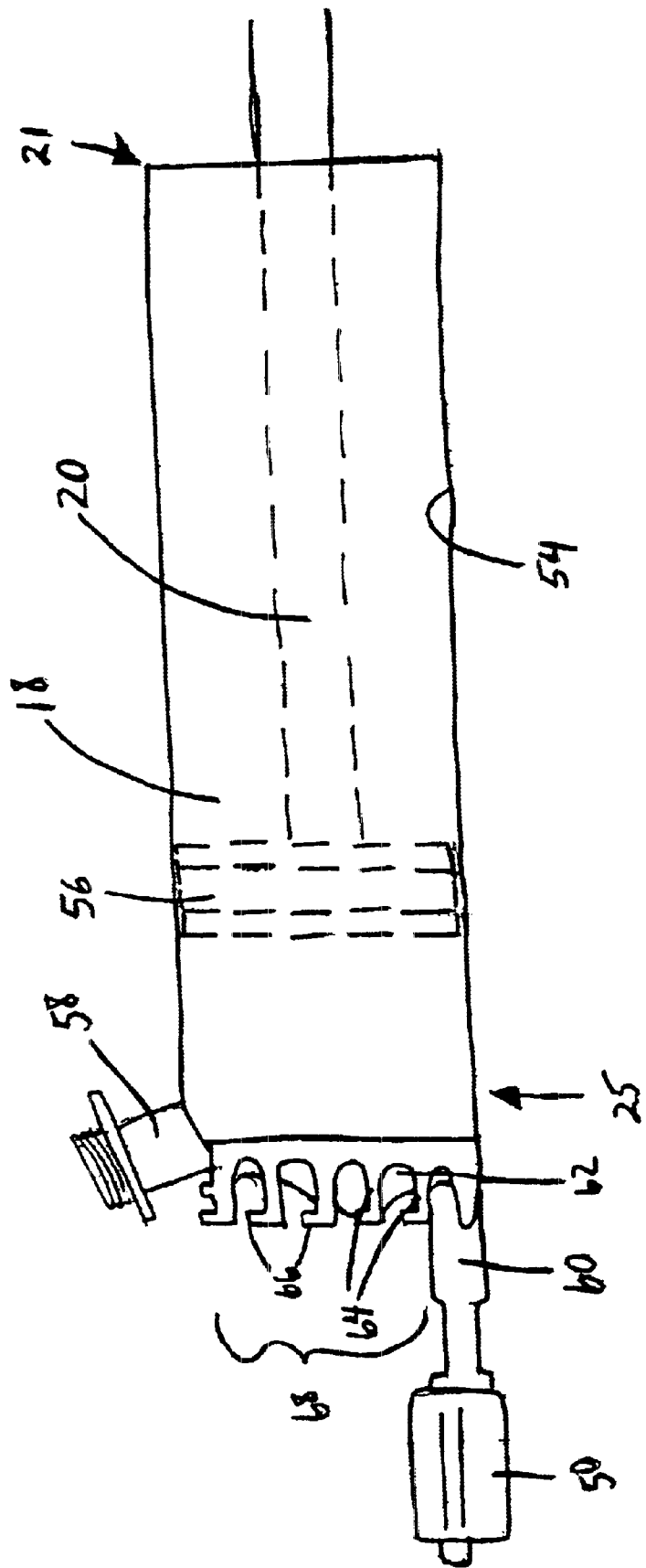
FIG. 3 is a cross-sectional view of the syringe body of the angiographic injector system in accordance with a preferred embodiment of the present invention.

Referring to FIG. 3, in a preferred embodiment the syringe body 18 of the injector subassembly 12 is cylindrically shaped, although alternate shapes, such as an oval shape or various other shapes, can also be used. The preferred shape of the syringe body 18 is cylindrical because of its edge-free or smooth, non-interrupted inner surface 54 that forms an enhanced fluid-tight seal between the inner surface 54 of the syringe body 18 and the wiper 56 of the syringe plunger 20. The annular shape of the inner surface 54 also facilitates cleaning and prevents material build-up on the inner surface 54 during use of the device.

The aspect ratio of the syringe body 18 is of a very wide range. Preferably, the aspect ratio is a function of the force and stroke of the moving component of the syringe 18, typically the syringe plunger 20. The inside diameter of the syringe body 18 may be variable provided that the syringe plunger 20 properly mates with and is movable within the syringe body 18. Similarly, the outside diameter of the syringe body 18 can also be any suitable size that enables the syringe body 18 to fit into the syringe holder 16 or other similar holding device.

Other alternative syringe configurations and shapes may also be used with the device of the present invention provided that the syringe 18 remains symmetrical with uniform sealing forces. These attributes not only enhance syringe performance, but also facilitate the manufacture of such syringes. In addition, it is preferred that the syringe 18 has a fluid volume capacity within the range of 60 ml to 250 ml. However, the final syringe capacity, design and configuration will be based on its mode of activation or other design and system constraints.

Due to the structural support provided by the syringe holder 16, the body of the syringe 18 requires minimal, although adequate, structural strength. The distal portion 25 of the syringe 18 is configured to include reinforcing structures, such as ribs 64, to provide added structural integrity and strength to this portion of the syringe 18 and to better manage the axial force of the syringe plunger 20.

In a preferred embodiment, the syringe body 18 is transparent or translucent and made of polycarbonate. The transparent material allows a user of the device to view the contrast media or fluid within the syringe body 18 and visually detect the presence of air bubbles in the system. Alternatively, other comparable materials, such as PET, clarified polypropylene, SAN, amorphous nylon, styrene, tempered glass, acrylic or other materials having similar strength and transparency characteristics may also be used. In addition, it is preferred that the materials comprising the syringe body 18 permit the syringe 18 to be cleaned and resterilized after several continuous reuses. This material preference is based largely on user preference whereby a reusable version of the syringe body 18 is typically preferred over a single use type in order to reduce hospital or health care facility expenses.

Referring to the syringe 18 structure as shown in FIG. 3, the proximal end 21 of the syringe body 18 is open to allow insertion of the syringe plunger 20 therein. Since the syringe plunger 20 is connected to and driven by a motor located within the user-interface subassembly 14, the syringe body 18 is positioned in the syringe holder 16 so that the open end of the syringe body 18 is adjacent to the user-interface subassembly 14.

The distal portion 25 of the syringe body 18 is closed and includes an upper port 58 and a lower port 60. The upper port 58 is approximately 10 mm in length, having variable inside and outside diameters. The upper port 58 of the syringe 18 is aligned at a 10 degree angle toward the distal end 25 of the syringe body 18 to ensure a vertical position for the port. In contrast, the lower port 60 is positioned parallel to the syringe body 18 and has a central, longitudinal axis approximately 16.5 mm lower than the central, longitudinal axis of the syringe body 18.

As shown in FIGS. 1–3, the upper port 58 attaches to the one-way valve 24 of the contrast container spike 48 which is inserted into the radiographic material reservoir 22. During use, contrast material is drawn from the reservoir 22 through the check valve 24 and upper port 58 and into the pumping chamber of the syringe body 18. Preferably, the check valve 24 is a one-way valve and includes a weighted ball (not shown) positioned at its lower seated position within the chamber.

As the syringe plunger 20 pumps contrast media into the lower port 60, any air remaining in the syringe body 18 is pumped out of the upper port 58. The weighted ball in the check valve 24 is sufficiently heavy to permit the air to flow from the syringe body 18 into the reservoir 22 without lifting the ball to an upper seated position. Once all the air is removed from the syringe body 18, the contrast media will begin to flow into the upper port 58. The specific gravity of the contrast media together with the hydrodynamic interaction of the weighted ball will lift the ball to an upper seated position, essentially blocking the passageway from the upper port 58 to the reservoir 22 so that contrast media cannot flow back from the syringe body 18 into the reservoir 22.

The key features of the angiographic injector system 10 that regulate fluid flow and/or prevent system and patient contamination include, but are not limited to, the patient valve 26, check valve 38, one-way valve 24, high pressure tube 28 and stop-cock 32. As described above, the patient valve 26 prevents retrograde flow of patient fluid to the syringe 18. As such, the patient valve 26 ensures that the syringe 18 remains sterile.

In addition, the saline check valve 38 also controls fluid flow to maintain contamination-free fluid flow paths. In particular, the check valve 38 functions to prevent fluid from flowing back into the saline supply thereby further ensuring system sterility and patient safety.

Similar to the function of the patient valve 26, the one-way valve 24 is also designed to prevent back-flow of contrast material from the syringe body 18 to the reservoir 22 supply. In so doing, the one way valve 24 simultaneously manages air flow and pressure between the syringe 18 and reservoir 22. In particular, during a purge function, the one way valve 24 passively recognizes when all the air has been removed from the system and, further, maintains the syringe pressure at a separate level from the reservoir pressure.

In addition to controlling fluid flow, the three-way stop-cock 32 of the present invention is also designed to minimize patient trauma during use of the injector system 10. The three-way stop-cock 32 includes three discrete positions that controllably regulate fluid flow to and from the patient. In a first position the stop-cock 32 prevents fluid from flowing into or out of the patient. However, this particular arrangement allows medications and/or fluid to be, respectively, either injected into or aspirated from the high pressure tube 28 through the patient medication port 34.

In a second position, the stop-cock 32 is open to allow fluid to flow from the high pressure tube 28, via the stop-cock 32, through the catheter connection 30 and into the patient. The stop-cock 32 is typically located in its second position during an imaging procedure that requires the injection of contrast media into the patient.

The third position of the stop-cock 32:provides a fluid flow path from the patient medication port 34, through the catheter connection 30 and ultimately to the patient. It is the third position of the stop-cock 32 that enables an operator of the device to inject or aspirate medications and/or fluids, respectively, into or from the patient. This particular feature allows additional diagnosis or treatments without having to create a separate injection site in the patient. As such, no additional patient trauma results from these supplementary procedures.

Another feature of the device of the present invention that reduces or eliminates system and/or patient contamination is the high pressure tube 28. The high pressure tube 28 is designed to be of sufficient length so that a relatively large volume of fluid separates the catheter connection 30 from the patient port 33. The volume of fluid and length of tubing prevents or significantly reduces the potential migration of contaminants from the patient site to the syringe body 18. Therefore, the patient valve 26, check valve 38, one-way valve 24, high pressure tube 28 and stop-cock 32, together with the particular design of the remaining system 10 components, significantly reduce or prevent system and patient contamination during one or more injection procedures.

Referring to FIGS. 1–3, the lower port 60 of the syringe body 18 includes an interconnection luer 50 used to connect and disconnect the single use portion 46 of the device of the present invention to the multiple use portion 44. In a preferred embodiment, the interconnection luer 50 is a rotating polycarbonate high pressure luer with locking collar that allows the used and/or contaminated single use components 46 to be quickly and easily removed and replaced with sterile components. Alternatively, other similar high-pressure capable connectors may also be used to form a connection between the single use portion 46 and the multiple use portion 44 of the angiographic injector system 10.

The inside diameter of the interconnection luer 50 is approximately 2.2 mm. Preferably, the interconnection luer 50 has as large a diameter as possible so as to reduce fluid flow restrictions between the single use portion 46 and the multiple use portion 44. In a preferred embodiment, the interconnection luer 50 is fabricated from a transparent or translucent material, such as polycarbonate, ABS or other similar materials, to allow for improved visualization of the fluid path and easy detection of any air contained within such path.

Referring to FIG. 3, the closed, distal end 25 of the syringe body 18 forms a frustroconical end wall 62. The frustroconical end wall 62 slopes at an angle of approximately 126 degrees from vertical and includes a rounded vertex having a radius of approximately 6.35±0.25 mm. The conical shape of the end wall 62 helps to direct fluids and gases to the appropriate ports 58, 60 during the set-up procedure and pumping function of the system 10.

Located on the exterior surface of the end wall 62 are one or more ribs 64. The ribs 64 are approximately 2.54±0.13 mm in thickness and are spaced approximately 2.54 mm apart. As shown in FIG. 3, the ribs 64 include flanges 66 that extend perpendicular to the longitudinal axis of the syringe body 18. The thickness of the ribs 64 in combination with the flanges 66 is approximately 3.56±0.13 mm. The ribs 64 and flanges 66 are positioned on the exterior surface of the end wall 62 so as to form a flat face 68.

In a preferred embodiment, there are seven ribs 62 extending transversely across the end wall 62. In addition to rendering an attractive, ornamental appearance to the syringe body 18, the ribs 64 also provide a structural, reinforcing function. Additional structural integrity is needed at the distal end 25 of the syringe body 18 to withstand the force exerted by the syringe plunger 20 and contrast media during the injection procedure.

Figure 5:
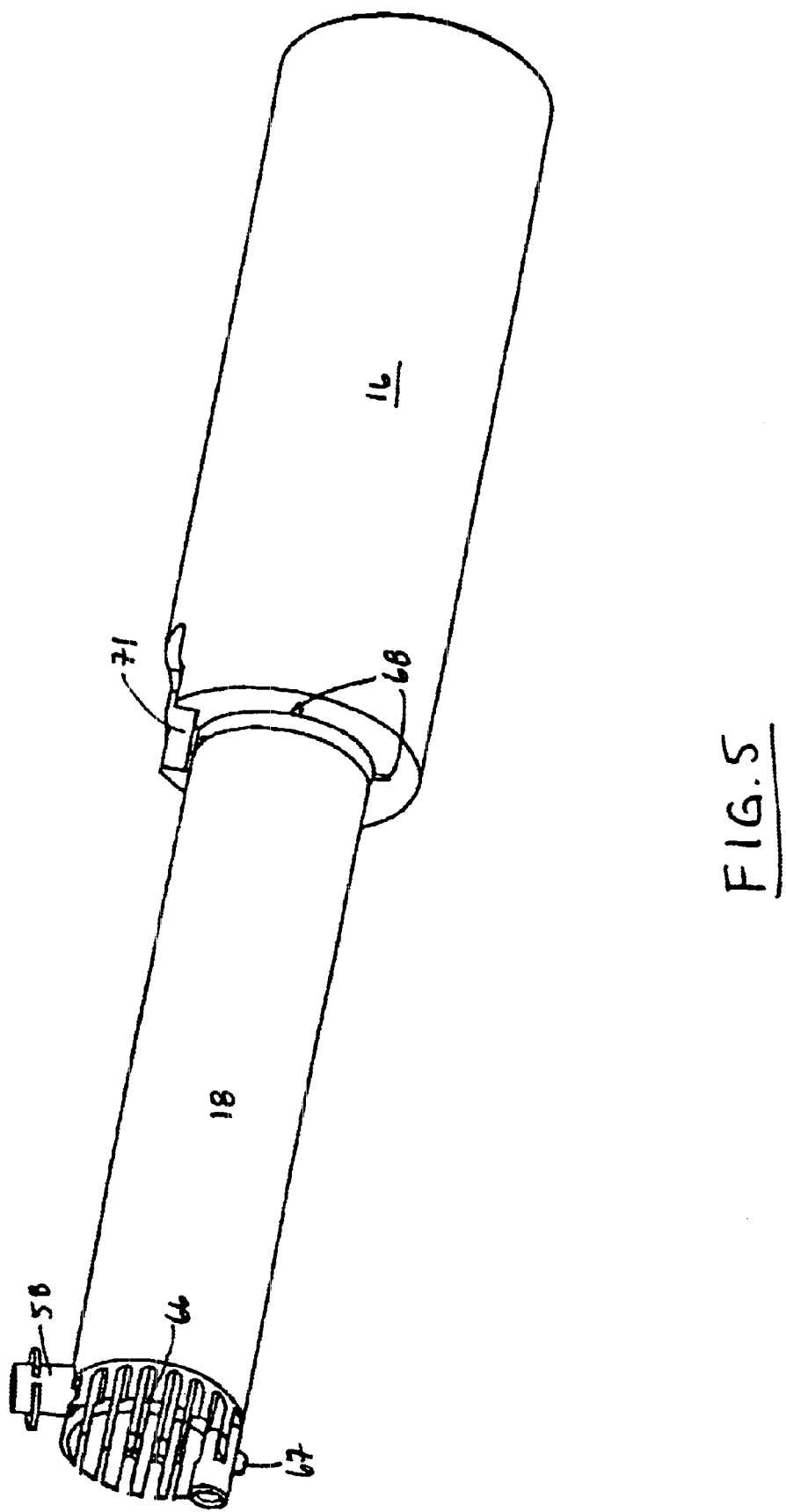
FIGS. 5 and 6 are perspective views of the syringe body partially positioned in the syringe holder in accordance with a preferred embodiment of the present invention.

The combination of ribs 64 and flanges 66 may also be used as a keying feature or structure to ensure that the proper syringe body 18 and accessories are used with the angiographic injector system 10 of the present invention. For example, in one embodiment, shown in FIGS. 4 and 5, the flanges 66, ridge 67 and notch 69 of the syringe body 18 mate with complimentary notches 68 and projections 70 located on the syringe holder 16. Further, the upper port 58 of the syringe body 18 fits into the groove 71 of the syringe holder 16 as an additional mating or keying feature of the present invention.

Although the preferred keying feature includes a combination of notches and projections, alternative keying or indexing embodiments can also be used. For example, in one embodiment, the keying feature comprises only the flanges 66, ridge 67 and upper port 58 on the syringe body 18 and the mating notches 68 on the syringe holder 16. In an alternate embodiment, the keying feature simply comprises the notch 69 and projection 70 located on the syringe body 18 and syringe holder 16, respectively. The quantity, pattern, shape and location of keying features can also be varied and still be within the scope of the present invention. In addition, similar mechanical indexing or keying configurations that are well-known in the art can also be used to ensure that the correct syringe body 18 is used with the angiographic system 10 of the present invention.

The mechanical fit between the syringe body 18 and syringe holder 16 prevents a user of the device from installing an incompatible syringe onto the system 10. In addition, due to the direct relationship between the syringe design and the procedure to be performed, the keying feature of the present invention also prevents the wrong kit configuration from being used with the wrong injector system set-up.

Figure 6:
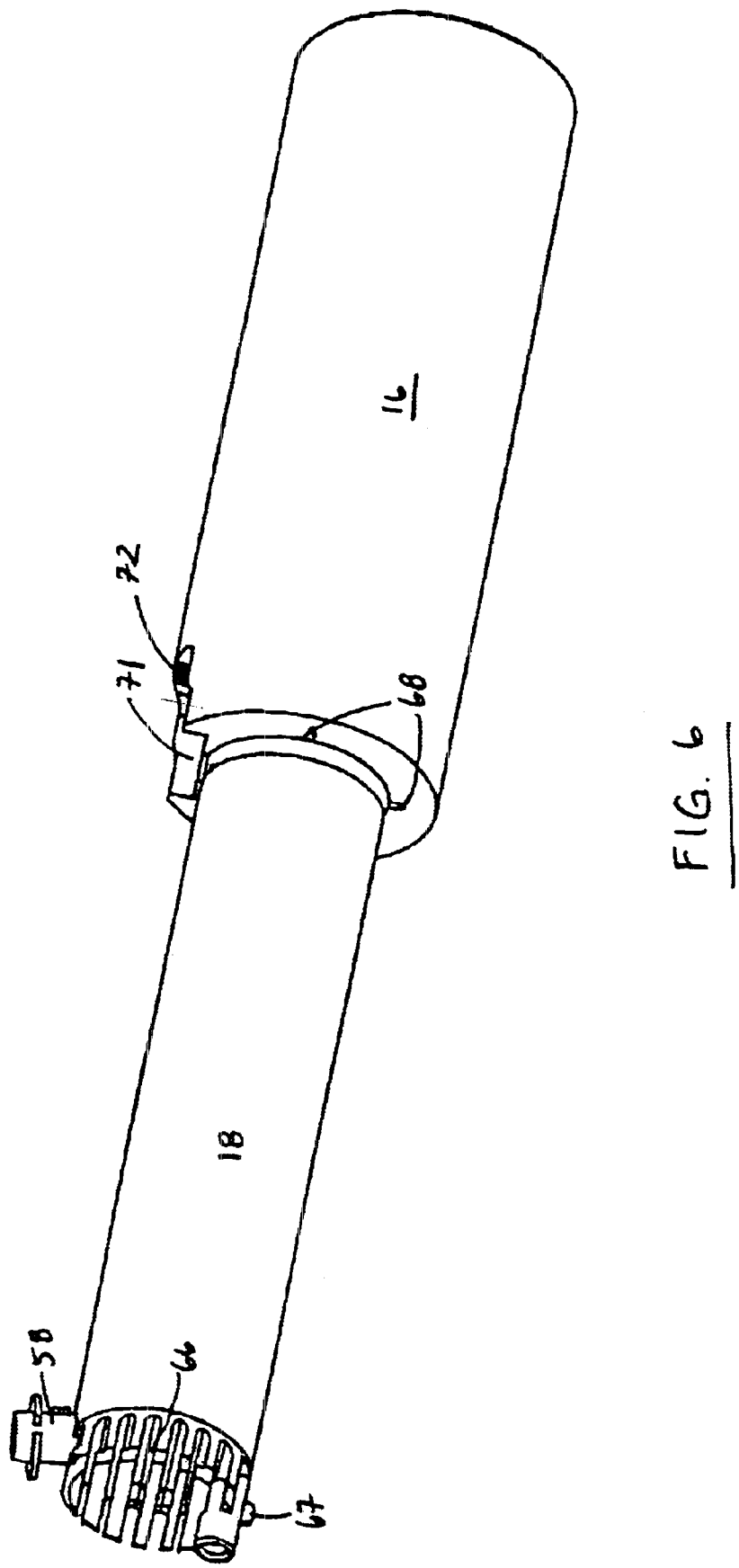

In addition to mechanical means, electrical means can also be used to ensure that the system 10 is correctly set-up and used. For example, in one embodiment of the present invention shown in FIG. 6, the projections and/or notches on the syringe body 18 contact switches or sensors 72 on the syringe holder 16. The switches or sensors 72 send a signal, such as a digital or analog signal, to the user interface subassembly 14 (not shown) indicating that the proper syringe body 18 is being used. If an operator of the device attempts to use an incompatible syringe. 18 with the system 10, the sensors 72 prevent the system 10 from functioning until a system-compatible syringe 18 is located in the syringe holder 16.

The sensors 72 are also used to distinguish whether the syringe 18 is a single-use syringe or a multiple use syringe. If the syringe 18 is single-use, the system 10 features prevent the syringe 18 from being used beyond a single patient or case. In contrast, if the syringe 18 is reusable, the system 10 tracks or counts the number of cases and shuts down when the syringe 18 reaches its maximum use. The system 10 then alerts the operator to change the syringe 18 and prevents continued operation of the device until the used syringe 18 has been removed and a new syringe 18 is installed on the system 10. In one embodiment of the device of the present invention, the syringe plunger 20 automatically disconnects from the syringe body 18 when the syringe 18 has been used for the maximum number of uses. The used/contaminated syringe 18 must be replaced with a new, sterile syringe 18 before the syringe plunger 20 and system 10 continue to operate.

One embodiment of the present invention utilizes sensors or switches to track syringe use via movement of the syringe plunger 20. For example, sensors, located along the length of the syringe holder 16, sense and track the movement of the syringe plunger 20 as it moves from the proximal end 21 toward the distal end 25 of the syringe body 18 during the injection procedure. By tracking the syringe plunger 20 movement, the system 10, together with information entered by an operator, is capable of tracking the volume of fluid injected into a patient. Upon completion of the procedure, the system operator terminates the case, for example, by pressing the "End Case" key or button. As such, the system 10 tracks and/or counts this as one use of the syringe 18. After the fifth use (or maximum number of uses) of the syringe 18, the system 10 notifies the operator that the syringe 18 has been used it maximum number of uses. At this point, the operator may either replace the syringe 18 with a new, sterile syringe or over-ride the system message and continue using the existing syringe 18.

In an alternate embodiment, when the system 10 reaches the maximum number of syringe reuses, the system 10 stops operating and notifies the operator via the display on the interface subassembly 14 that the syringe 18 must be replaced with a new, sterile syringe 18. After the syringe 18 is replaced, the system 10 continues to function. Thus, for this embodiment of the present invention, the operator may not over-ride or by-pass the system message and, as such, must replace the existing syringe 18.

In yet another embodiment of the present invention, sensors can also be positioned on the system 10 to track or monitor the number of turns of the motor that controls plunger 20 movement. According to this embodiment, each turn of the motor is directly related to a specific distance of plunger 20 travel within the syringe body 18. Further, the amount of plunger movement also directly corresponds to a specific volume of fluid injected or displaced by the syringe 18. As described above, upon completion of the injection procedure, the system operator terminates the case by pressing the "End Case" key. As a result, the system 10 can track the number of completed cases/procedures by counting the number of times an operator performs an "End Case" function.

The switches and sensors may also be used in combination with the accessory components of the angiographic system 10, such as the interconnection luer 50, high pressure tube 28, saline spike 52, etc. As with the syringe body 16, the switches and sensors ensure that only system compatible accessories are used with the device of the present invention. In addition, the switches and sensors also track or count the number of cases or patients to prevent reuse of the accessories beyond their recommended use. Data or information on the accessories is communicated to the operator via the interface subassembly 14.

Other electrical and/or software means, in addition to sensors and switches can also be used with the device 10 of the present invention. For example, in an alternate embodiment, a small memory or identification chip is placed in a cable or sensor on the syringe holder 16. The chip communicates with the interface subassembly 14 and identifies whether a system compatible syringe 18 or kit is installed. As with the sensors, the chip together with the interface subassembly 14 prevent the system 10 from functioning until a system-compatible syringe 18 or kit is installed.

In a further embodiment, a bar-code is applied to the syringe body 18. A bar-code reader, located on the syringe holder 16 or other suitable location on the system 10, reads the bar-code on the syringe body 18. The bar-code information is then processed by the user interface subassembly 14 and displayed to the operator. The system 10 cannot be activated to begin an injection procedure unless the bar-code reader reads an appropriate bar-code or, in other words, until a compatible syringe body 18 is installed in the syringe holder 16. In addition to preventing incompatible syringes 18 from being used, the bar-code and bar-code reader are also used to indicate whether a single use or multiple use syringe 18 or kit has been properly connected to the system 10.

In addition to switches, sensors and memory/identification chips, other similar devices such as antennas, optics or similar devices can also be used to track the number of uses for a particular component and to verify that the correct components are used with the angiographic system 10 of the present invention.

An example of an antenna device used on the present invention is similar to conventional anti-theft tag devices used in stores. In one embodiment of the present invention, the antenna is located on the syringe body 18 and the resonance circuit is located onto the syringe holder 16. When the syringe body 18 is positioned in the syringe holder 16, the resonance circuit receives a signal from the antenna indicating that the correct syringe body 18 is being used on the system thereby allowing the system to operate. However, if the syringe body 18 does not have an antenna or has an antenna that emits an incorrect signal, then the resonance circuit prevents the system from operating until the appropriate syringe is installed.

In another embodiment of the present invention, an optical switch or detector is used to detect the presence of the syringe body 18 in the syringe holder 16. In particular, a beam of light emitted from the syringe holder 16 onto a detector sends a signal to the user interface indicating that the syringe holder 16 is empty. When a syringe body 18 is positioned in the holder 16, the syringe body 18 breaks the beam of light thereby indicating that the syringe holder 16 is loaded. In an alternate embodiment, the syringe body 18 also includes a switch triggered by a beam of light. As such, when the syringe body 18 is positioned in the syringe holder 16, the switch signals to the user interface that the syringe holder 16 is loaded and that the appropriate type of syringe 18 is being used on the system.

Although only the above-described embodiments of an antenna and optics device has been disclosed in detail, it should be understood that alternative, state of the art antenna and optics devices can also be used with the angiographic system and still be within the scope of the present invention.

The injector system 10 of the present invention also includes additional features directed to user convenience and user/patient safety. In particular, the injector system 10 has numerous safety features that prevent the system 10 from being used in the event of an operational error. One such feature is the resume function. During normal operation and upon completion of a procedure, the system 10 is shut-down by a system operator using the appropriate shut-down sequence of steps, including completion of an "End Case" action. Following this procedure, a subsequent powering-up of the system 10 only allows a user to re-start the system 10 and requires new disposable components to be installed on the system.

In contrast, when system operation is interrupted or the system is improperly shutdown, due to encountering certain errors, a brown-out or a loss of power, system 10 intelligence assesses the shut-down situation and provides the operator with two options concerning restart of the system 10. In other words, re-starting the system 10 following a system shut-down without performing an "End Case" action by the system operator requires the operator to select either "restart" or "resume." As described above, the "restart" feature is equivalent to beginning a new procedure or operation and requires existing components to be removed and new disposable components to be installed on the system.

In contrast, the "resume" feature provides the operator with a choice of whether or not to continue with the procedure or case after an improper power-down is encountered. Thus, the resume feature allows a user to return to the main screen on the user-interface and continue the procedure without having to replace any system components. However, the input parameters and the case totals for the injection fluids and the last injection values are lost and re-set to zero.

The resume function also enables an operator from erroneously removing disposable system components prior to completion of a procedure. Typically, at the end of a case, the system 10 requires an operator to remove the disposable components prior to initiation of a new procedure or case. However when the system is shut-down (as described above) prior to completion of the procedure, the operator may simply continue the procedure by activating the resume feature of the system 10. The resume function allows the system 10 to function and the procedure to continue without requiring the operator to perform a standard initialization of the system or replace any of the disposable components.

Another novel feature of the injector system 10 of the present invention is the one-shot refill option. In one embodiment of the present invention, the one-shot refill option enables the manufacturer or operator of the device to preprogram unique keystrokes corresponding to predetermined fluid increments or volumes frequently selected during various injection procedures. These preprogrammed keystrokes are then saved and stored in the memory system of the user-interface subassembly 14. This feature enables the system 10, on demand via a single keystroke, to automatically refill the syringe 18 with the specified volume of fluid corresponding to the particular key selected by the operator. In other words, the one-shot refill option allows an operator of the device 10 to quickly and efficiently fill a syringe 18 with a specified volume of fluid using a single key stroke.

In an alternate embodiment, the one-shot refill feature is available to a system operator via an automatic mode or a manual mode. In the automatic mode, an operator activates the one-shot refill option by pressing a button on the system 10. Although other conventional or state of the art triggering devices can also be used with the present invention, in the spirit of convenience and brevity, the one-shot refill feature will be described with reference to a button as its method of activation. Upon activation, the one-shot refill feature automatically fills the syringe 18 to its maximum volume or to a volume equivalent to the amount of fluid remaining in the reservoir/bottle 22. As such, fluid fill volumes are based on syringe 18 capacity and remaining reservoir 22 supply amounts.

In contrast, the manual mode of the one-shot refill feature enables an operator to manually control the fill volume of the syringe 18. This mode of operation requires an operator to press and hold the one-shot refill button until the syringe 18 is filled to the desired volume of fluid. As such, the operator is able to accurately and efficiently fill the syringe 18 to a variety of customized volumes. Therefore, this particular feature of the present invention not only enhances user convenience but also reduces both patient and health care facility costs.

The device of the present invention also includes additional variations to the one-shot refill feature. In addition to controlling refill volumes, the system also enables an operator to preprogram specific times for the refill function to occur. For example, during a saline injection, the patient manifold 26 is open to allow saline to flow from the saline subassembly 37 to the high pressure tube 28. In this configuration, the patient manifold 26 is closed with respect to the syringe 18 fluid flow path. As such, the operator can preprogram the one-shot refill feature to automatically refill the syringe 18 when saline is being dispensed by the system 10.

As another example, the operator can preprogram the one-shot refill option to occur during specific hours throughout the day. Alternatively, the one-shot refill option can also be pre-programmed to automatically occur when the supply of fluid in the reservoir 22 reaches a set minimum volume. Other similar preprogramming alternatives, though not specifically disclosed, are also included within the scope of the present invention.

Another feature of the injector system 10 is its fluid management system whereby the injector system 10 automatically monitors or tracks the amount of fluid dispensed from the system 10. Conventional injector systems require I.V. poles or similar devices to hold fluid supply reservoirs, such as contrast media bottles/bags. Though readily available, these devices are typically inconvenient to use, have a tendency to tip and frequently cause the supply reservoir to become disconnected from the injector system.

Figure 7:
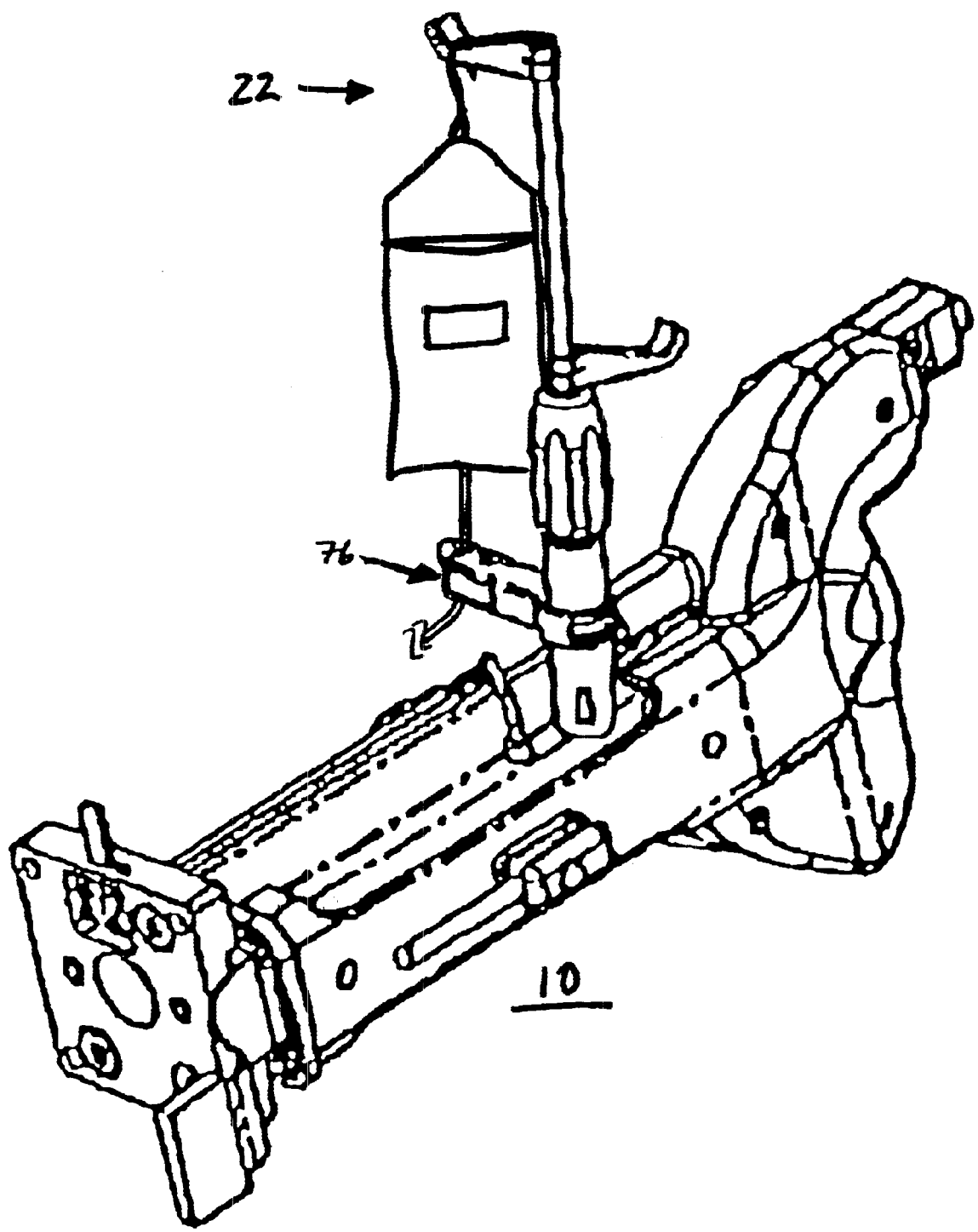
FIG. 7 is a perspective view of the reservoir in accordance with a preferred embodiment of the present invention; and, FIG. 8 is a perspective view of sensors used to track the volume of fluid used on the system in accordance with a preferred embodiment of the present invention.

In contrast, the injector system 10 of the present invention includes a component specifically configured to hold or contain a supply of fluid. In one embodiment of the invention, shown in FIG. 1, the component is the reservoir 22 containing a volume of fluid. In another embodiment, shown in FIG. 7, the component is also the reservoir 22, however, for this embodiment, the reservoir 22 is designed to also accommodate a variety of containers, such as bottles, bags, etc., housing the various fluids used during injection procedures. As such, the reservoir 22 of the present invention allows for a more controlled allocation of system fluids and contributes to overall system convenience and safety for a user of the device.

The overall system fluidics, and in particular the fluid sensing and fluid tracking features of the present invention, enable the system 10 to efficiently and effectively manage the amount of fluid used on the system 10. For example, conventional injection systems rely on the operator's ability to determine when a bottle 22 needs to be replaced. Often, to avoid the possibility of running out of fluid during a procedure, thereby requiring the procedure to be repeated, an operator will prematurely replace the bottle 22. This practice creates added hospital or health care facility expense due to the high cost of wasted contrast media or other injection fluids. This particular problem is addressed by the following fluid sensing and fluid tracking features which accurately monitor and efficiently manage fluid use.

In one embodiment of the device of the present invention, the system 10 includes a feature that allows contrast media to be used from the radiographic material reservoir/bottle/bag 22 for one or more procedures or uses. The reservoir 22 and system 10 are designed to be of sufficient size and optimum configuration so as to permit multiple users to draw into the contrast material supply without contaminating the patient(s) or compromising the sterility of the supply in the bottle 22 or syringe 18. Specifically, the system 10 is designed to allow the syringe 18 to "infinitely" or continuously draw in contrast media from the radiographic material reservoir/bottle 22. When the bottle 22 is empty, the user of the device simply discards the empty bottle 22 and attaches a full bottle 22 of contrast media onto the contrast container spike 48. At this point, the operator may continue with a current, on-going procedure or, alternatively, may begin a new procedure. Moreover, with respect to an on-going procedure, none of the associated system components needs to be disconnected or replaced since the system is able to maintain a sterile fluid path during the bottle replacement procedure.

Figure 8:
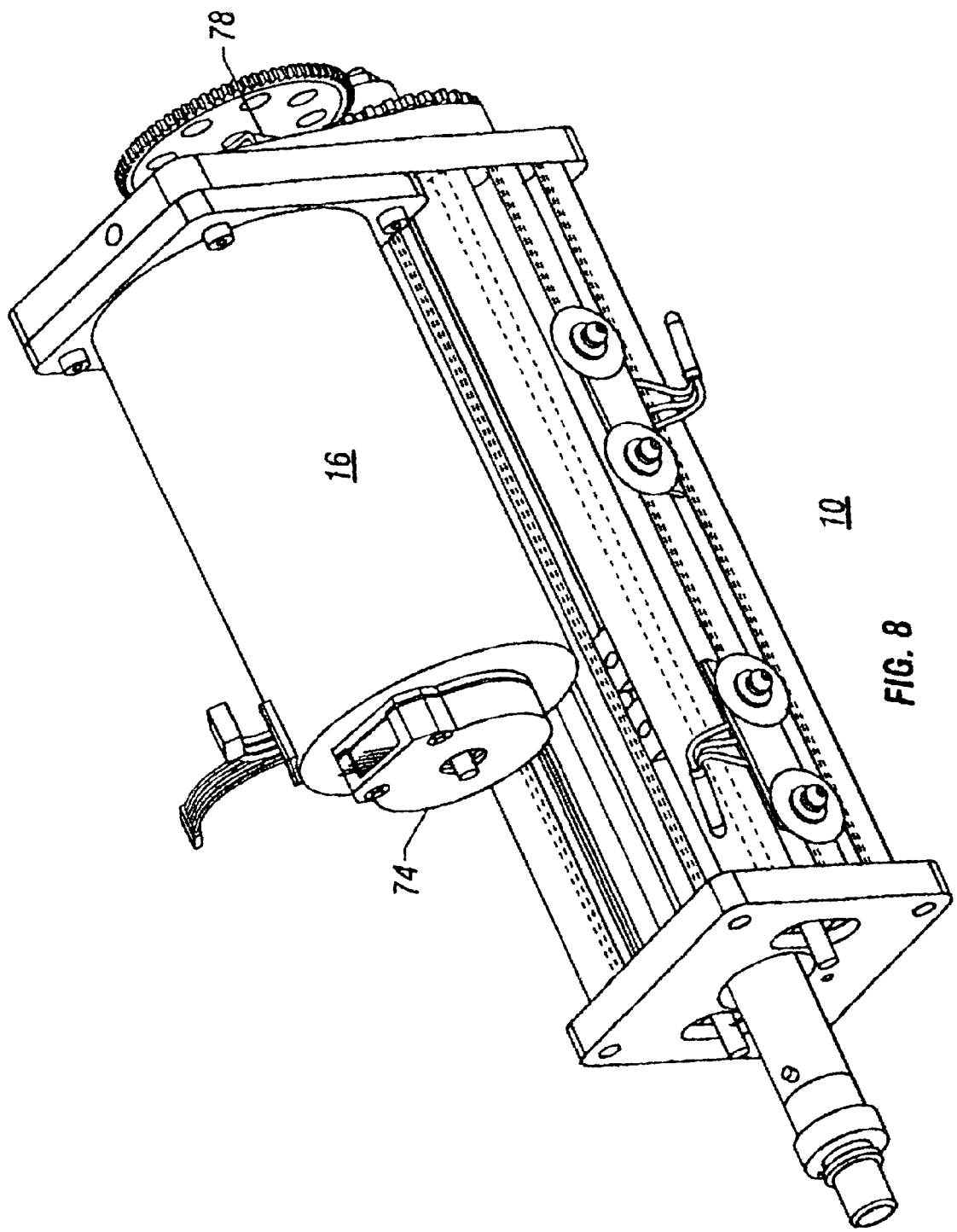

In another embodiment, shown in FIG. 8, an encoder or sensors 74 located on a motor in combination with a gear assembly 76 attached to a potentiometer track the volume of fluid used on the system 10 via the number of turns of the motor. This data, which may be used with optional information input by the operator for the bottle size/volume of the injection fluid, allows the system 10 to continuously and accurately calculate the volume of fluid remaining in the bottle 22. Alternatively, the system 10 can be completely automated whereby even the bottle size/volume is detected using bar-codes and bar-code readers, sensors or similar devices, and the information is then automatically processed by the system 10.

Fluid volume and usage can be tracked by other methods as well. For example, in an alternate embodiment of the present invention, shown in FIG. 7, IR (infra-red) detector-emitter pairs or sensors 76 are located along the contrast container tubing. During use of the system 10, the sensors 76 sense the presence of fluid within the spike 48 or tubing and alert the operator of the system 10, via the user-interface subassembly 14 (not shown), when the container 22 is empty and/or when all the air is purged out of the system. In addition, the sensors 76 may also warn the operator if air bubbles are present in the tubing between the valve 24 and the spike 48 (not shown). The user-interface subassembly 14 notifies the operator of the status of the fluid via the system display.

In another embodiment of the present invention, sensors or similar devices are positioned at various levels along the supply reservoir 22. The sensors continuously track the fluid level in the reservoir 22 and send this information to the user-interface subassembly 14. The information is them processed by the system 10 and communicated to the operator via the system display. Alternatively, this feature may also include an alarm, visual and/or audible, to alert the user to the amount of fluid remaining in the bottle 22. As a result, the system 10 is able to accurately and effectively control the timing when a bottle 22 needs to be replaced.

Method of Use

Prior to initial use, the system 10 of the present invention must be appropriately set-up by the user or operator of the device. The operator of the system 10 first enters patient parameters, such as age, sex, height, weight, etc., into the user-interface subassembly 14. Next, the operator selects the type of procedure, such as radiology, cardiology, etc., to be performed. The operator is then presented, via the display, a selection of target areas commonly associated with the particular procedure selected. For example, if the operator selects a cardiology procedure, the operator is given, via the display, a selection of target areas including right coronary, left coronary, left ventricle, aorta, etc. After the injection type is selected, the operator inputs the particular function, such as a contrast media injection or a saline flush, to be performed by the system 10. After all patient and system information is programmed into the user-interface subassembly 14 of the injector system 10, the operator of the device arms the system 10.

Once the system 10 is turned on, it guides the user through a series of steps to install components and/or accessories onto the system purge out air and prime the system 10 with fluid. This system set-up and prime must be completed prior to connecting the patient's catheter to the catheter connection 30. During the system prime, the syringe plunger 20 automatically draws in the appropriate volume of fluid into the syringe body 18 based upon the parameters entered by the user of the device. Next, the syringe plunger 20 pushes the fluid in the syringe body 18 toward the distal end 25 of the syringe 18. As the fluid flows into the lower port 60 of the syringe 18, excess air is expelled via the upper port 58. After all the air is removed from the syringe body 18, the weighted ball of the one-way valve 24 is pushed by the fluid into a sealing position so as to substantially block the fluid from back-flowing into the supply reservoir 22. Upon exiting the lower port 60 of the syringe body 18, the fluid flows into the patient manifold 26. The pressure from the fluid biases the spool valve of the patient manifold 26 causing the valve to change states so that the lower port 50 of the syringe body 18 connects to the patient port 33. The fluid then flows from the patient port 33 into the high pressure tube 28, through the three-way stop cock 32 and into the catheter connection 30, thereby completing the system prime.

Next, the system 10 notifies the user, via the display on the user-interface subassembly 14, that the system is ready for use. The user connects the patient's catheter to the catheter connection 30 and arms the system 10 to begin the injection procedure. A volume of fluid is then injected at either a fixed rate or variable rates proportionally controlled by the user, into the patient. The values for the rate and volume of the fluid are the preferred default values as calculated by the system 10 based upon the input parameters. If preferred, a user can input different values for the rate and volume of fluid by manually entering the numbers into the user-interface subassembly 14.

At the end of the injection procedure, the user terminates the case/procedure. In one embodiment of the present invention, after disconnecting the patient from the device, the syringe plunger 20 automatically disconnects from the system 10.

The foregoing description addresses embodiments encompassing the principles of the present invention. The embodiments may be changed, modified and/or implemented using various types of arrangements. Those skilled in the art will readily recognize various modifications and changes which may be made to the invention without strictly following the exemplary embodiments and applications illustrated and described herein, and without departing from the scope of the invention which is set forth in the following claims.

What is claimed is:

1. An injector subassembly used with an injector system, said injector subassembly comprising:
    a single use portion; and
    a multiple use portion;
    said single use portion fluidly connected to said multiple use portion, said single use portion including a high pressure tube connected to a catheter connection and said multiple use portion including a syringe connected to a fluid supply reservoir; said syringe and said high pressure tube being in fluid communication at a predetermined period of operation.

2. The injector subassembly of claim 1 wherein said single use portion includes a three-way stop-cock connecting said high pressure tube to said catheter connection.

3. The injector subassembly of claim 2 wherein said three-way stop-cock includes a patient medication port.

4. The injector subassembly of claim 1 wherein a length of said high pressure tube is related to a pressure drop along said length.

5. The injector subassembly of claim 1 wherein said high pressure tube is made of PVC.

6. The injector subassembly of claim 1 wherein said single use portion includes a patient manifold that connects said syringe to said high pressure tube.

7. The injector subassembly of claim 6 wherein said patient manifold includes a spring biased spool valve which normally connects a pressure transducer to a patient port.

8. The injector subassembly of claim 6 wherein said single use portion includes a pressure transducer connected to said patient manifold.

9. The injector subassembly of claim 8 wherein said single use portion includes a saline subassembly attached to said pressure transducer.

10. The injector subassembly of claim 9 wherein said saline subassembly includes a saline check valve, saline tubing, saline spike and saline supply.

11. The injector subassembly of claim 1 wherein said multiple use portion includes a one-way valve connecting said syringe to said fluid supply reservoir.

12. The injector subassembly of claim 11 wherein said multiple use portion includes a fluid container spike connecting said one-way valve to said fluid supply reservoir.

13. The injector subassembly of claim 11 wherein said one-way valve includes a weighted ball that when seated in a lower position permits air to flow from said syringe body and when seated in an upper position prevents fluid from flowing from said syringe body to said fluid supply reservoir.

14. The injector assembly of claim 1 wherein said multiple use portion is reused up to approximately five times.

15. The injector assembly of claim 1 wherein said multiple use portion is reused on one or more patients without cleaning or sterilizing said multiple use portion between each use.

16. The injector subassembly of claim 1 wherein said single use portion is cleaned and sterilized after being used on said patient or case.

17. The injector subassembly of claim 16 wherein said single use portion is reused after said single use portion is cleaned and sterilized.

18. The injector subassembly of claim 1 wherein said syringe is transparent.

19. The injector subassembly of claim 1 wherein said syringe is made of polycarbonate.

20. The injector subassembly of claim 1 wherein said syringe repeatedly draws in fluid from said supply reservoir.

21. The injector subassembly of claim 1 wherein said single use portion is supplied to a user of said subassembly as a kit.

22. The injector subassembly of claim 1 wherein said multiple use portion is supplied to a user of said subassembly as a kit.

23. A multiple use syringe for use in an injection system, said multiple use syringe comprising:

a syringe body having a distal end, a proximal end and a pumping chamber; and a syringe plunger located in said pumping chamber and movable along a path from said distal end to said proximal end of said syringe body, said syringe plunger connected to and controlled by a user-interface assembly whereby said syringe plunger automatically disconnects from said syringe body when said syringe body has been used for a maximum number of uses.

* * * * *